United States Patent
Murray et al.

(10) Patent No.: US 7,708,180 B2
(45) Date of Patent: May 4, 2010

(54) SURGICAL FASTENING DEVICE WITH INITIATOR IMPREGNATION OF A MATRIX OR BUTTRESS TO IMPROVE ADHESIVE APPLICATION

(75) Inventors: Michael A. Murray, Bellevue, KY (US); Douglas J. Turner, Cincinnati, OH (US); John V. Hunt, Cincinnati, OH (US); Mark S. Ortiz, Milford, OH (US); David N. Plescia, Cincinnati, OH (US); Frederick E. Shelton, IV, Hillsboro, OH (US); Ronald J. Kolata, Raleigh, NC (US); Robert H. McKenna, Bountiful, UT (US); Craig N. Faller, Milford, OH (US); James W. Voegele, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 349 days.

(21) Appl. No.: 11/558,208

(22) Filed: Nov. 9, 2006

(65) Prior Publication Data
US 2009/0120994 A1    May 14, 2009

(51) Int. Cl.
*A61B 18/14*    (2006.01)
(52) U.S. Cl. ............ 227/175.1; 227/179.1; 227/180.1; 227/19
(58) Field of Classification Search ........... 227/175.1, 227/179.1, 180.1, 19
See application file for complete search history.

(56) References Cited

U.S. PATENT DOCUMENTS

| | | | | |
|---|---|---|---|---|
| 5,441,193 A * | 8/1995 | Gravener | ........... | 227/176.1 |
| 5,468,253 A | 11/1995 | Bezwada et al. | | |
| 5,503,638 A * | 4/1996 | Cooper et al. | ........... | 623/11.11 |
| 5,752,965 A * | 5/1998 | Francis et al. | ........... | 606/151 |
| 5,902,312 A * | 5/1999 | Frater et al. | ........... | 606/148 |
| 6,325,810 B1 * | 12/2001 | Hamilton et al. | ........... | 606/151 |
| 6,503,257 B2 * | 1/2003 | Grant et al. | ........... | 606/151 |
| 6,592,597 B2 * | 7/2003 | Grant et al. | ........... | 606/151 |
| 6,656,193 B2 * | 12/2003 | Grant et al. | ........... | 606/151 |
| 6,942,675 B1 * | 9/2005 | Vargas | ........... | 606/153 |
| 7,032,799 B2 * | 4/2006 | Viola et al. | ........... | 227/175.1 |
| 7,238,195 B2 * | 7/2007 | Viola | ........... | 606/219 |
| 2001/0023354 A1 * | 9/2001 | Blatter et al. | ........... | 606/153 |
| 2002/0165559 A1 * | 11/2002 | Grant et al. | ........... | 606/139 |

(Continued)

*Primary Examiner*—Brian D Nash
(74) *Attorney, Agent, or Firm*—Frost Brown Todd LLC

(57) ABSTRACT

A material comprising a matrix or a buttress is impregnated with an adhesive initiator and is used with a surgical stapling device and an adhesive. The tissue and material are stapled together, and a knife in the surgical stapling device cuts the tissue and the material. The adhesive is applied across the cut and sets up or polymerizes to seals the cut when the adhesive contacts the adhesive initiator. The surgical stapling device can place the staples in a linear, arcuate, or circular array, and can anastomose luminal tissue. The methods of use can include stapling luminal tissue end to end, stapling two portions of material onto ether side of tissue, and stapling two portions of tissue onto a portion of material. Additionally, a portion of adhesive filed material can be stapled onto one side of portion of tissue and the adhesive initiator impregnated material can be stapled onto the other. Cutting the material and tissue provides a path for the adhesive across the cut, and catalyzes the adhesive from contact with the adhesive initiator.

17 Claims, 14 Drawing Sheets

U.S. PATENT DOCUMENTS

| | | | |
|---|---|---|---|
| 2004/0148010 A1* | 7/2004 | Rush | 623/1.13 |
| 2004/0190975 A1 | 9/2004 | Goodman et al. | |
| 2005/0021026 A1* | 1/2005 | Baily | 606/51 |
| 2005/0145671 A1* | 7/2005 | Viola | 227/175.1 |
| 2005/0165444 A1* | 7/2005 | Hart et al. | 606/213 |
| 2005/0184121 A1* | 8/2005 | Heinrich | 227/175.1 |
| 2005/0192628 A1* | 9/2005 | Viola | 606/219 |
| 2005/0228446 A1 | 10/2005 | Mooradian et al. | |
| 2005/0230453 A1* | 10/2005 | Viola | 227/176.1 |
| 2006/0025813 A1* | 2/2006 | Shelton et al. | 606/205 |
| 2006/0025816 A1* | 2/2006 | Shelton | 606/215 |
| 2006/0085032 A1* | 4/2006 | Viola | 606/219 |
| 2006/0085036 A1* | 4/2006 | Viola | 606/228 |
| 2006/0111738 A1* | 5/2006 | Wenchell | 606/186 |
| 2006/0212050 A1* | 9/2006 | D'Agostino et al. | 606/151 |
| 2006/0235469 A1* | 10/2006 | Viola | 606/219 |
| 2007/0102452 A1* | 5/2007 | Shelton et al. | 222/191 |
| 2007/0102453 A1* | 5/2007 | Morgan et al. | 222/191 |

* cited by examiner

SURGICAL FASTENING DEVICE WITH INITIATOR IMPREGNATION OF A MATRIX OR BUTTRESS TO IMPROVE ADHESIVE APPLICATION

FIELD OF THE INVENTION

The present invention relates, in general, to tissue fastening devices, and more particularly, to tissue fastening devices using a combination of staples and adhesives.

BACKGROUND OF THE INVENTION

Adhesives and sealants have been contemplated to supplement or replace staple based transaction devices for many years. The primary challenges in accomplishing this are control of getting the adhesive into the correct location at the correct time as well as preventing it from adhering the stapler itself to the treatment site. Adhesives have proven themselves as great short term bonding/sealing mechanisms. Staples on the other have proven themselves a very good long term tissue apposition mechanisms. Therefore the best of both worlds would be to use staples to fasten and adhesives in combination with adhesive initiators to seal the juncture of tissue or tissue cuts.

The primary challenge in the creation of a hybrid adhesive/ staple deploying system is the positioning of the adhesive into only the areas of desired adhesion and controlling where the adhesive bonds to the area.

Closure Medical is conducting an FDA clinical trial using a cyanoacrylate adhesive as an internal vascular tissue sealant and internal surgical adhesive. Some adhesives such as the cyanoacrylates, stick well to tissue, but like metallic fasteners, the fastener itself can become a local barrier to tissue regrowth through the fastener. For internal body use of surgical adhesives, the adhesive is used sparingly, not on top of the wound as in external use, but actually in the cut areas of the wound. By minimizing the glue areas across the wound, the surgeon is assured of maximum areas of tissue regrowth and minimal areas of the adhesive barrier. As the tissue regrows together and heals, the adhesive areas within the wound are encapsulated with healed tissue. Thus, internal adhesives are ideal for short term needs to hold cut tissue together so that healing can occur, and can remain as a long term fastener to provide additional strength to the healed tissue. Additionally, the adhesives can be biocompatible, bioabsorbable, and/or flexible, inside the body.

Tissue fastening can be either short term or long term duration. Short term duration fasteners can include a bandage, tape, removable staples, removable suture, adhesives, or absorbable stitches that are meant to provide temporary support until natural healing can occur.

Longer duration fasteners must remain in or on the body, possibly for the life of the patient. Longer duration fasteners include biocompatible implantables such as suture, staples, clips, tacks, clamps, pins, and the like. These long duration fasteners could be inserted subcutaneously in a surgical procedure and, after the patient has healed, cannot be removed without additional surgery. Longer term fasteners can provide short term and long term reinforcement for high force loads that can be 200-400% of normal forces. These high force loads could be caused by violent vomiting, coughing, and, in some cases, chronic overeating. For chronic overeaters that have undergone bariatric surgery to create a small stomach pouch, it is highly likely that a patient will "overload" the new pouch by attempting to eat the same large portions of food imbibed before the surgery.

Adhesives have been used topically as a short term fastener for wound repair. Closure Medical has developed a 2-octyl cyanoacrylate compound with a long carbon chain (eight carbons) that is biocompatible, has good bonding strength, and has received FDA approval for topical use. For short duration topical wound closure, the edges of the wound are brought together and at least one layer of the adhesive is applied along the surface of the wound line to form a barrier that holds the wound edges together. The cyanoacrylate adhesive also acts as a microbial barrier, keeping bacteria out and is eventually removed. Cyanoacrylate adhesives are described in United States Application 20040190975 by Goodman et al. which is herein incorporated by reference in its entirety.

Closure Medical is conducting an FDA clinical trial using a cyanoacrylate adhesive as an internal vascular tissue sealant and internal surgical adhesive. Some adhesives such as the cyanoacrylates, stick well to tissue, but like metallic fasteners, the fastener itself can become a local barrier to tissue regrowth through the fastener. For internal body use of surgical adhesives, the adhesive is used sparingly, not on top of the wound as in external use, but actually in the cut areas of the wound. By minimizing the glue areas across the wound, the surgeon is assured of maximum areas of tissue regrowth and minimal areas of the adhesive barrier. As the tissue regrows together and heals, the adhesive areas within the wound are encapsulated with healed tissue. Thus, internal adhesives are ideal for short term needs to hold cut tissue together so that healing can occur, and can remain as a long term fastener to provide additional strength to the healed tissue. Additionally, the adhesives can be biocompatible, bioabsorbable, and/or flexible, inside the body.

Adhesives used to hold buttress materials to linear and circular surgical devices are known, such as that taught in U.S. Pat. No. 6,592,597 to Grant et al. entitled "Foam Buttress For Stapling Apparatus" as well as U.S. 2005/0228446 by D. Mooradian et al. entitled "Circular Stapler Buttress Combination", both of which are incorporated by reference herein in their entirety.

Consequently, a significant need exists for a surgical device that can staple and cut tissue, can simply and easily place an adhesive initiator at desired sites to attract and set an adhesive about a junction or cut line in the tissue, can prevent unwanted adhesive migration away from the desired adhesion areas, and can ensure a seal across the cut line or tissue junction.

BRIEF SUMMARY OF THE INVENTION

The invention overcomes the above-noted and other deficiencies of the prior art by providing a surgical stapling instrument for clamping and stapling tissue. The surgical stapling instrument has a handle, and a first and a second opposed tissue clamping members connected to the handle. At least one of the first and second opposed tissue clamping members are movable between an open position for receiving tissue and a closed position for stapling tissue therebetween. The first clamping member includes a plurality of staples disposed therein in an array, and the second clamping member comprises an anvil for forming the staples. Also provided is a first portion of biocompatible material containing an adhesive initiator. The first portion of biocompatible material is releasably attached to one of the first and second opposed tissue clamping members. A second portion of biocompatible material contains a fluid adhesive and is releasably attached to the other of the first and second opposed tissue clamping members. A knife is operably movable between the first and a second opposed tissue clamping members. Wherein when the tissue is clamped and stapled, the knife cuts the tissue and the first and second portions of material and the adhesive is released. The cut provides a passage for migration of the adhesive from the second portion of material to the adhesive initiator to initiate hardening of the adhesive across the cut.

In another aspect of the invention, a method for securing a first and a second portion of tissue together with a plurality of staples and an adhesive is disclosed. The method includes a first step of placing a portion of material containing an adhesive initiator between a first portion and a second portion of tissue. The second step comprises, clamping the material and the first and second portion of tissue between a first and a second clamping member of a surgical device with at least an edge of the material exposed. The third step includes stapling the two portions of tissue together with the portion of material therebetween with the plurality of staples in an array. The last step includes applying an adhesive about the exposed material and the two portions of tissue to initiate the adhesive and secure the two portions of tissue together.

In yet another aspect of the invention, a method for sealing a first portion and a second portion of tissue together with a plurality of staples and an adhesive is disclosed. The first step comprises clamping the first portion and the second portion of tissue between a first portion of buttress and between a second portion of buttress with a surgical stapling device. The first portion of buttress contains an adhesive initiator. The second step is stapling the first portion and the second portion of tissue between the first portion of buttress and the second portion of buttress by applying a plurality of fasteners in an array. The third step is cutting the tissue and the buttress about the array of staples with a knife of the surgical device. And the last step is sealing the cut tissue and buttress together by applying an adhesive across the cut and initiating the adhesive by contacting the adhesive with the adhesive initiator in the first portion of buttress.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Surgical stapling devices are well known in the art for clamping onto tissue and placing a plurality of fasteners in an array into the tissue. Knives can also be included in the surgical stapling device and are used to sever or cut tissue within the array of staples. Such stapling devices can be circular, linear, arcuate, or any other shape and are commonly used to resects or transect tissue, can perform an anastomosis on luminal structures such as intestines, can resects lung tissue, or be used in any one of a number of other surgeries. Using an adhesive initiator impregnated material (such as a buttress or matrix) in combination with a stapling device and an adhesive offers advantages as will be described below.

Figure 1:
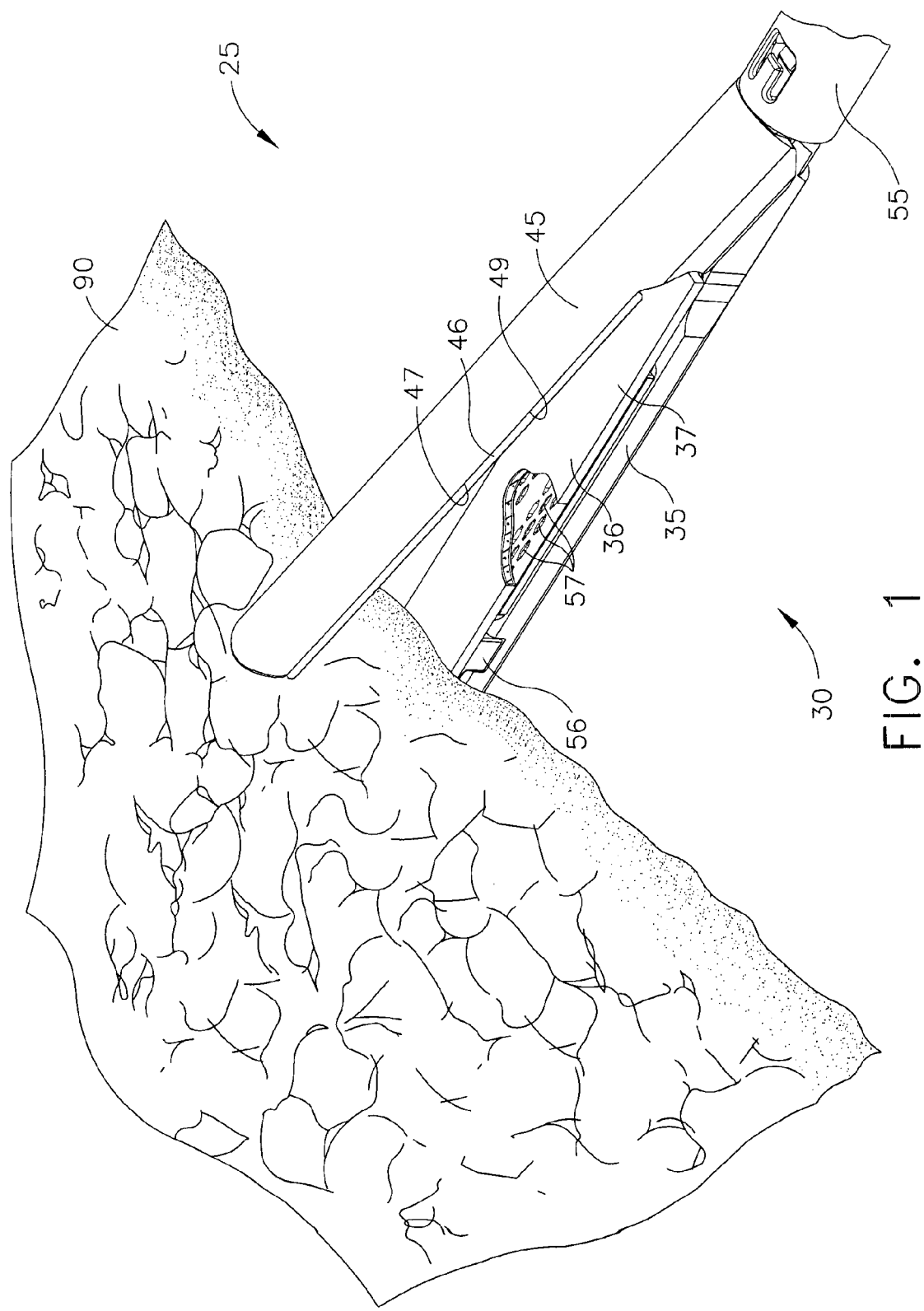
FIG. 1 is an isometric view of an end effector of a surgical stapling device with a first portion of a buttress material containing an adhesive attached thereto on a one jaw and a second portion of a buttress material containing an adhesive initiator on the another jaw.

In FIG. 1, an end effector 30 of a surgical stapling device 25 such as an endocutter is shown prior to clamping on lung tissue 90 and placing a plurality of surgical fasteners such as staples therein. The surgical stapling device 25 can have an end effector 30 at a distal end of shaft 55 comprising a pair of moveably opposed tissue clamping members at least one of which is moveable. The tissue clamp members may comprise a fixed first clamping member 35 and a movable second clamping member 45 movable from an open position to a closed position to clamp and staple tissue 90 therebetween. A handle 32 (not shown) can extend proximally from the shaft 55 and could be operably attached to the end effector 30 to clamp and unclamp the first clamping member 35 and second clamp member 45 onto tissue, and to staple and cut the clamped tissue when fired. The surgical stapling device 25 can include buttressing or matrix materials to buttress and strengthen the staple line formed in tissue which can comprise a first portion of material 36 releasably attached to the first clamping member 35 and a second portion of material 46 releasably attached to the second clamping member 45. The first and second portions of material 36, 46 could be biocompatible, and the first portion of material 36 may contain an adhesive initiator 38 that can initiate setting or polymerization of an adhesive on contact. The second portion 46 of material can contain a biocompatible polymer adhesive 48 that reacts or polymerizes from contact with the adhesive initiator 38.

The first clamping member 35 can have a removable staple cartridge 56 containing a plurality of surgical fasteners or staples 57 therein covered by the first portion of material 36. The second clamping member 45 may contain a plurality of opposing staple pockets 47 for the formation of the staples 57 therein and releasably covered by the second portion of material 46 containing an adhesive 47. When the second clamping member 35 is clamped on tissue, the staple pockets 47 align with the array of staples 57 in the cartridge 56, and when the surgical device 25 is fired, the staples 57 are driven upwards through the tissue and the materials to form the staples 57 in the staple pockets 47.

Figure 2:
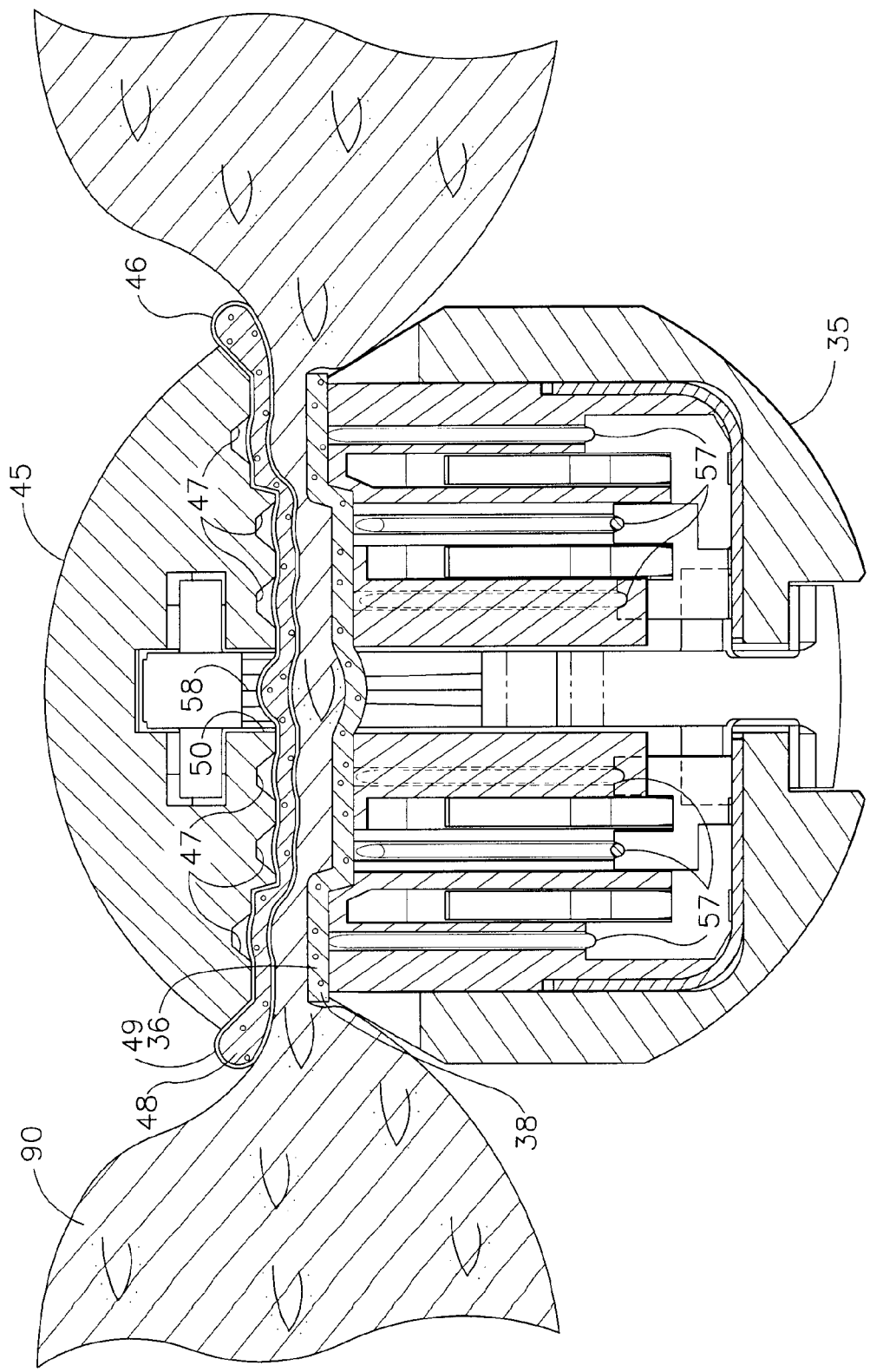
FIG. 2 is a cross sectional view of the end effector of FIG. 1 clamped on tissue.

FIG. 2 is a cross sectional view of the end effector 30 clamped on lung tissue 90. The staples 57 are positioned in the removable cartridge 56 in an array of six parallel longitudinal rows in alignment with the pockets 47. For this example, the rows of staples 57 are staggered. A knife 58 is located between the innermost rows of staples 57 and when the surgical device is fired, the knife 58 travels longitudinally along the first and second clamp members 35,45, to cut both the tissue 90 and the first and second portions of material 36,46 clamped therebetween. For this example, the second portion of material 46 may be an open cell sponge structure filled with the fluid adhesive 48, and sealed by a cuttable surface 49. The cuttable surface 49 can create a fluid filled, deformable second portion of material 46 that can be cut or penetrated to release the adhesive 48 sealed therein. Cuttable surface 49, for example, can be placed on the second portion of material 46 as a dip, a spray coating, a vacuum deposited coating, a skin formed by a molding process, an injection molded coating and the like. Suitable materials for the cuttable surface can be absorbable or non-absorbable, and can include materials such as but not limited to butyrate or polyethylene rubber, silicone or plastic material, such as, for example, polyvinyl chloride, polyethylene, polyurethane, natural or nitrile rubber, polylactic acid, polyglycolic acid, polyglactin, polydioxanone, polyglyconate, whey protein, cellulose gum, starch, gelatin or any combination thereof. Cuttable surface 49, is not limited to these processes and materials and by way of example, can comprise an adhesive filled sponge structure sealed within a pouch 49a about the second portion of material 46 or any other means to seal the glue filled second portion of material 48. As shown in FIG. 2, the sealed second portion of material 46 is clamped between the clamping members 35,45 and is bulging laterally out of each side of second clamping member 45 and into a knife slot 50. The bulging or ballooning is from the clamping pressure on the incompressible fluid adhesive 48 sealed into the second portion of material 46. The first portion of material 36 can contain an adhesive initiator 38 that is combined with the first portion of material 36. The combination of an adhesive initiator 38 and a first portion of material 36 may not be limited to the molding process, and can include, by way of example, a coating on the first portion of material 38.

Figure 3:
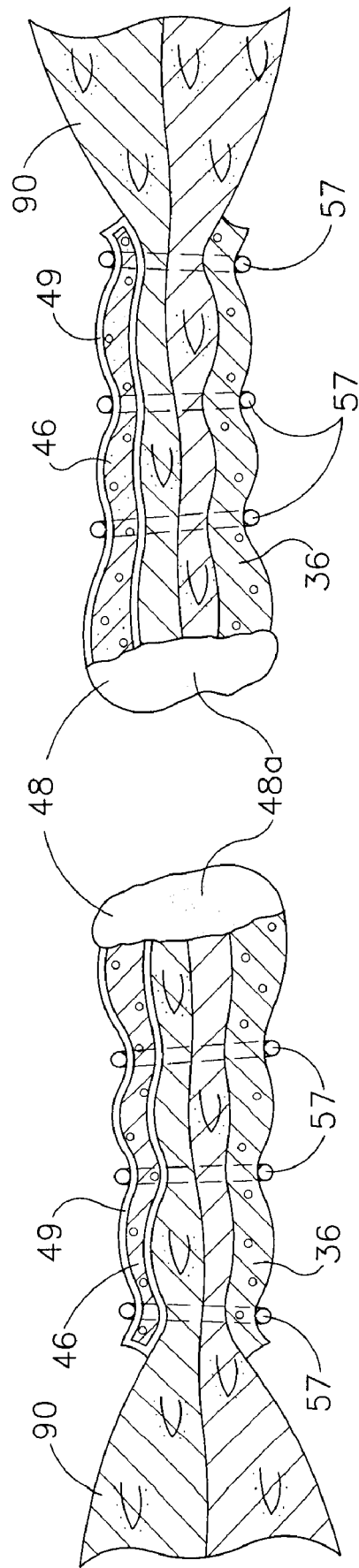
FIG. 3 is a cross sectional view of the cut and stapled tissue and buttress material of FIG. 2 showing the adhesive migrating across the cut tissue to contact the adhesive initiator in the second portion of a buttress material to initiate setting of the adhesive.

FIG. 3 shows the tissue 90 after being clamped, stapled, and cut with the surgical device 25. The stapling and cutting process can form six staggered rows of staples 57 in the compressed tissue 90, and can cut both the tissue 90 and the compressed first and second portions of material 36, 46. The cutting of the compressed second portion of material 46 with knife 58 may breach the sealed surface 49 of the second portion of material 46 and can release the pressurized fluid adhesive 48 sealed within. With the surface 49 breached, the glue 48 can migrate inward about the cut. The speed of the inward migration of the adhesive 48 can be controlled by the viscosity of the fluid adhesive 48 and, for this example, is timed to ooze out of the cut in the second portion of adhesive after the surgical device 25 has the first and second clamping members 35,45 opened to release the tissue 90 clamped therein. The formed staples 57 may continue to apply pressure on the first and second portions of material 36, 46 to continue migration of adhesive 48 from the second portion of material 46 after the surgical device 245 has been removed. In FIG. 3 the adhesive 48 has oozed or migrated over the cut in the tissue 90 to contact the adhesive initiator 38 in the first portion of material to create polymerized or set adhesive 48a across the cut. The polymerization process, once initialized, is shown migrating from the initial initiator contact site to convert all of the adhesive 48 into set adhesive 48a and to prevent migration of the adhesive 48 from the cut area. The above example uses materials and processes which will now be described in greater detail.

Buttress and Mesh Materials

Buttress and mesh materials are sheet-like fabric or foam reinforcing structures and are well known in the art for backing up staple or suture lines, and as hernia mesh support structures and the like. Buttress and mesh materials can be biocompatible to be implanted in the body, can be penetrated with surgical fasteners, and can be absorbable or non-absorbable. In the above example, two different portions of buttress material can used. The first portion of material 36 may be a closed cell foam buttress material containing an adhesive initiator 38, and the second portion of material 46 can be a sponge type open cell buttress material containing a fluid polymer adhesive 48 sealed within by sealed surface 49.

Buttress materials can include VICRYL™, produced by Ethicon, Inc., Somerville N.J., "DEXON™", produced by Sherwood-Davis and Geck, St. Louis, Mo., and TEFLON™, produced by E.I. DuPont de Nemours & Co., Wilmington, Del. Additionally, other buttress materials include animal material such as tanned bovine pericardium, biocompatible elastomers such as .epsilon.-caprolactone glycolide produced by Ethicon Inc., Gargrave, England, or any one of a number of suitable buttress materials. Suitable .epsilon.-caprolactone glycolide materials or foams are described in U.S. Pat. No. 5,468,253 hereby incorporated by reference.

Alternately, the first or second portion of material 36, 46 could be a mesh structure or matrix 337 (not shown) having a plurality of openings 336. Such a matrix 337 could be a foam material containing openings 336, or a mesh, or a threadlike structure. The first or second portion of material 36, 46 could include porosities or at least one capillary action inducing feature or a wicking feature to draw adhesive 48 or initiator 38 to or into the material. These wicking features can include a pore, a void, a weave, a bubble, an open cell, a mesh, or any other feature that can induce capillary action or wicking action. Wicking properties of structure 26 (not shown) can ensure openings 27 (not shown) remain clear of adhesive to allow tissue growth therethrough Thus, for example, the first portion of material 36 can be a mesh structure coated in an adhesive initiator 38, and the second portion of material 46 could be a mesh structure surrounded by a viscous adhesive 48 and sealed within a pouch 49a.

In addition to the materials above, suitable absorbable materials for a mesh or buttress structure can include but are not limited to bioabsorbable materials such as polylactic acid, polyglycolic acid, polyglactin, polydioxanone, polyglyconate, whey protein, cellulose gum, starch, and gelatin. Non-absorbable materials suitable for mesh or buttress can include but are not limited to materials such as silk, nylon, polypropylene, braided polyester, polybutester, polyethylene, and polyetheretherketones (PEEK).

Thus, the above first portion of material 36 and second portion of material 46 could be a fibrous pad, a foam, a matrix, a mesh or any other structure that can contain an adhesive initiator 38 or an adhesive 48. The first portion of material 36 and second portion of material 46, can, for example, have wicking properties such that when placed on tissue, can wick adhesive 48 thereto.

Attaching Buttress and Mesh Materials to a Stapling Device

Buttress materials can be releasably attached to the surgical device 25 in a variety of ways such as but not limited to a releasable adhesive such as that described in U.S. Pat. No. 6,592,597 by Grant et al. which is hereby incorporated by reference in its entirety.

Additionally, other methods of attachment such as anvil carriers could be used such as that described in U.S. Pat. No. 6,656,193 by Grant et al. which is also hereby incorporated by reference in its entirety. The above methods of releasably attaching buttress materials are not meant to be limiting in any way and any other devices and methods of attachment are within the scope of the invention.

Adhesives

Adhesive 48 could be, but is not limited to polymerizable and/or cross-linkable materials such as a cyanoacrylate adhesive. The adhesive 48, for example, may be a monomeric (including prepolymeric) adhesive composition, a polymeric adhesive composition, or any other compound that can adhere to tissue. In embodiments, the monomer may be a 1,1-disubstituted ethylene monomer, e.g., an .alpha.-cyanoacrylate. When cross linked or polymerized, the cyanoacrylate can change from a liquid to a solid. Polymerized adhesives 48a for example, can be formulated to be flexible to rigid and could be spongy. If desired, adhesive 48 an be a single part or dual part adhesive, and/or can contain additives such as alternate compounds. Polymerization of the adhesive 48 can occur from, but is not limited to, exposure to moisture or adhesion initiators 104.

Adhesive Initiators

Particular adhesive initiators 38 for particular monomers may be readily selected by one of skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, base compositions, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents. Other examples of adhesives 48 and adhesive initiators 38 may be found in United States Application 20040190975 by Goodman et al. which is herein incorporated by reference in its entirety.

First Alternate Embodiment

Figure 4:
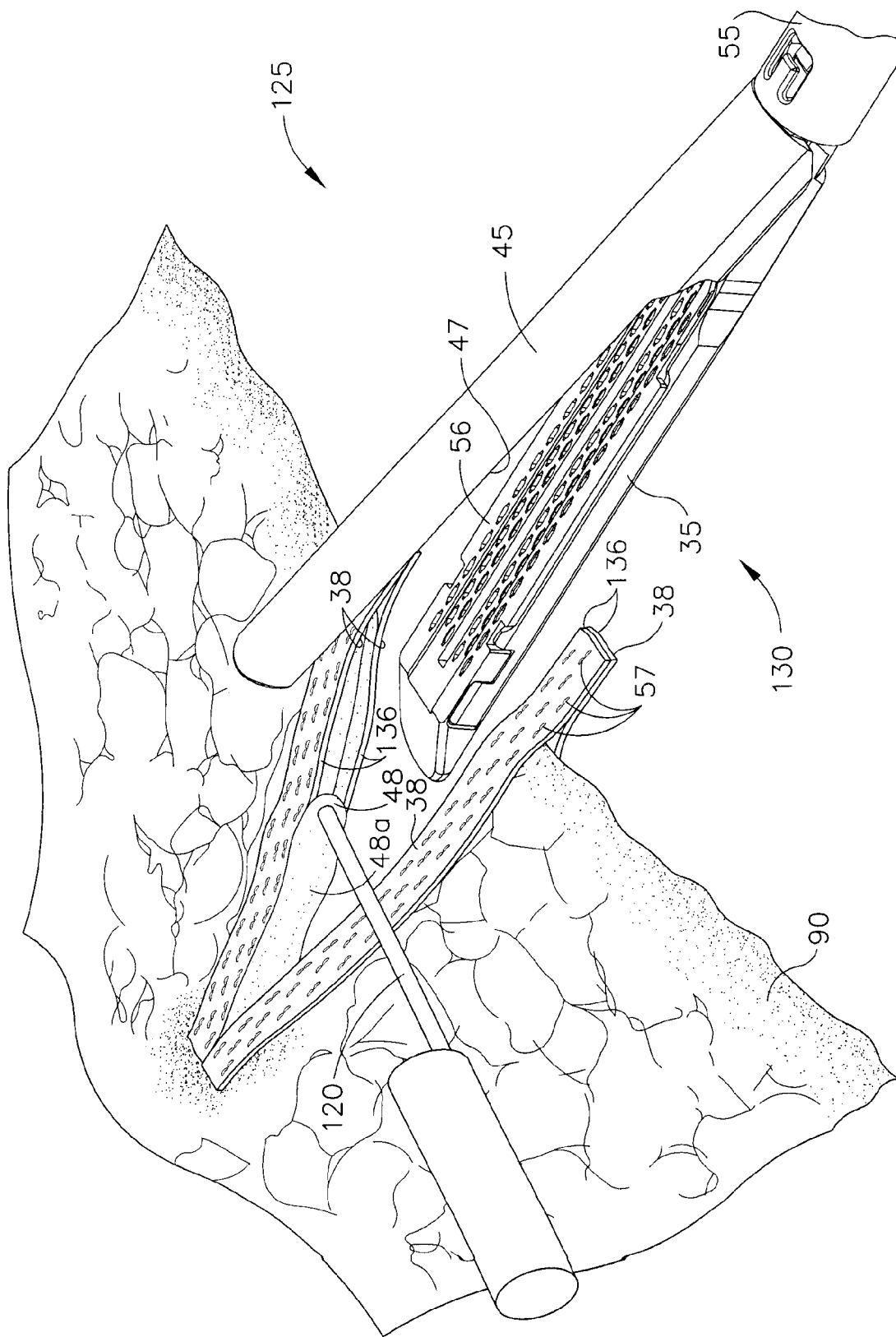
FIG. 4 is an isometric view of another surgical stapling device after stapling a first and a second portion of buttress material containing an adhesive initiator onto the tissue and with an adhesive applicator applying adhesive to the tissue and to the buttress with the adhesive initiator to initiate setting of the adhesive.

FIG. 4 shows an alternate embodiment of a surgical device 125 that is the above described endocutter that was combined with two releasable portions of an initiator material 136 that contain an adhesive initiator 38. In FIG. 4, the two releasable portions of initiator material 136 are shown stapled on lung tissue after the tissue is clamped, stapled, and cut between the first and second clamping members 35, 45 of the surgical device 125. The clamping and stapling and cutting process has stapled, cut, and released the two releasable portions of material 136 containing an adhesive initiator 38 onto the tissue 90. The releasable portions of initiator material 136 are buttress material and may prevent staple tear out in the thin frangible lung tissue.

Lung tissue comprises thin air sacs or bladders in combination with vascular structures to ensure the oxygenation of blood. As a consequence, severing or cutting lung tissue can include small bleeders and/or air leaks. In FIG. 4, an adhesive applicator 120 is shown applying adhesive 48 along the cut tissue 90 to ensure pneumostasis and hemostasis along the cut tissue. As the adhesive 48 contacts the adhesive initiator 38 in the releasable portions of initiator material 136, the adhesive 48 begins to convert to the polymerized or set adhesive 48a, and bonds to the cut tissue to create a seal. The set adhesive 48a can seal leaks and may be absorbable or non-absorbable.

Second Alternate Embodiment

Figure 5:
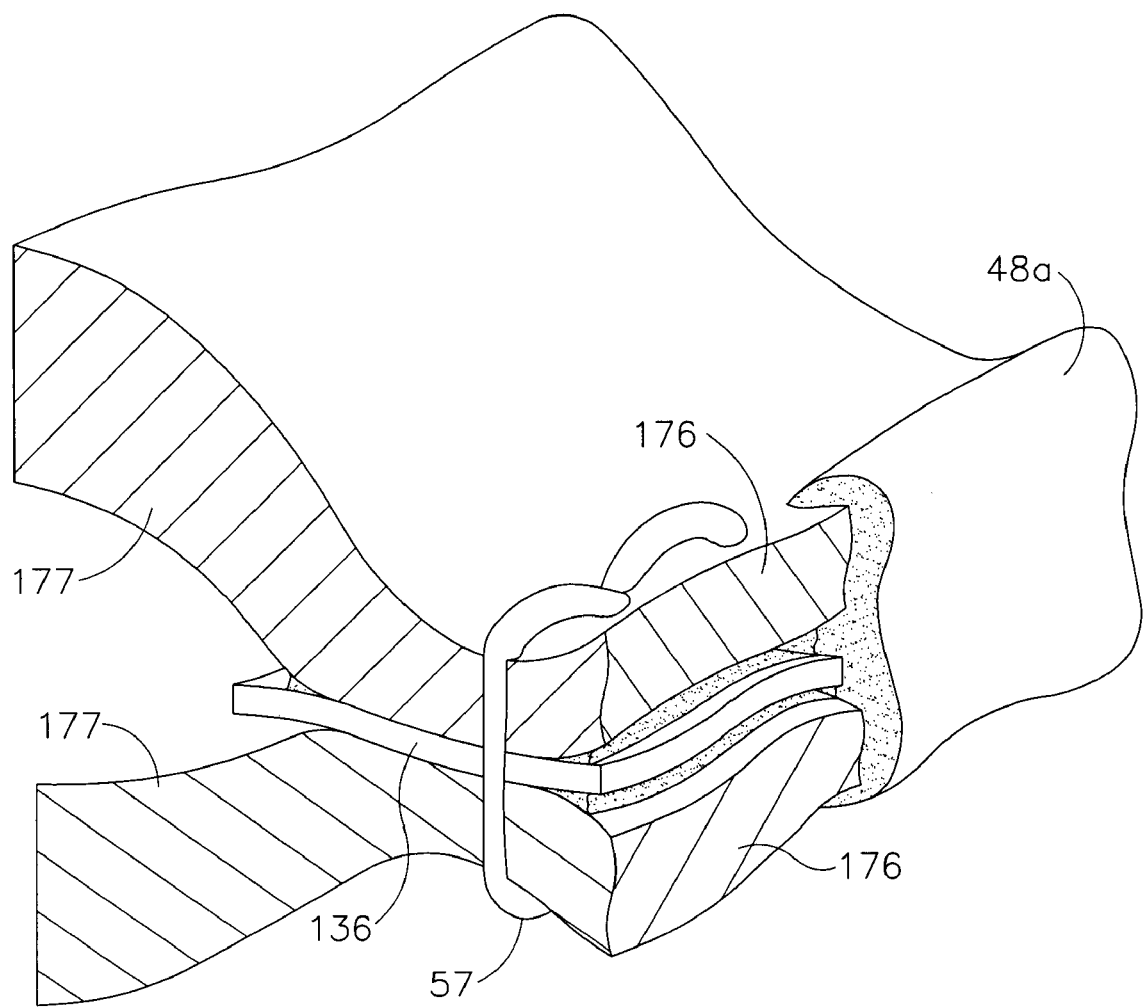
FIG. 5 is an isometric view of two portions of tissue stapled together and sandwiching a portion of buttress therebetween, and showing a polymerized adhesive applied to the cut tissue and polymerized by contact with the adhesive initiator.

FIG. 5 shows an alternate method of securing tissue with a stapling device, a single portion of initiator material 136, and the adhesive 48. As shown, a portion of initiator material 136 is placed between to tissue portions 177 and the tissue and initiator material 136 is clamped, stapled, and cut. A pair of cut edges 176 of the tissue 177 can then be coated with adhesive 48 from the adhesive applicator 120 (see FIG. 4), and the contact of the adhesive 48 with the adhesive initiator 38 in the initiator material 136 has polymerized or set the adhesive 48 into the set adhesive 48a shown. The single portion of material 136 can be a matrix, a mesh, or a foam buttress. A foam buttress material that can be compressed by clamping and stapling between irregular tissue materials and can expand to fill gaps between irregular tissue surfaces. This method of securing tissue can be used with the endocutter described above or with a circular stapler described below.

Circular Stapler with Dual Rings of Buttress or Matrix

Figure 6:
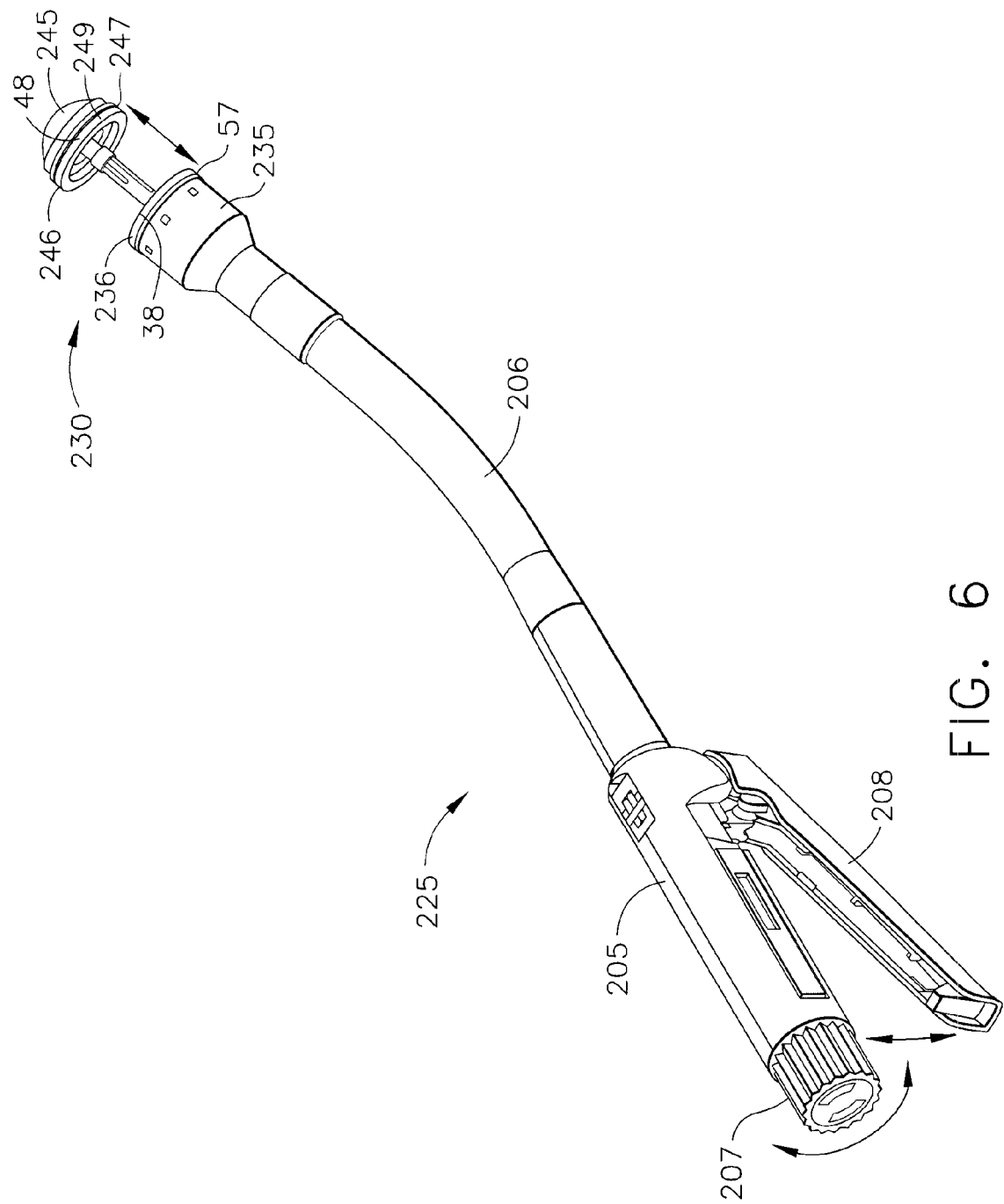
FIG. 6 is an isometric view of a circular stapler with a first portion of a buttress material containing an adhesive attached thereto on a fixed jaw and a second portion of a buttress material containing an adhesive initiator on a movable jaw in an open position.

FIG. 6 shows a circular stapler 225 that is commonly used to create an end-to-end resection of a first portion of intestinal tissue 210 (not shown) with a second portion of intestinal tissue 211 (not shown) in an end-to-end anastomosis. The circular stapler 225 has a handle 205, a shaft 206 extending distally therefrom, and a circular end effector 230 at a distal end of the shaft 206. Circular end effector 230 includes a fixed first clamp member 235 and a movable second clamp member 245 for clamping and stapling and cutting tissue therebetween. A first initiator ring 236 of foam buttress is releasably attached to the first clamp member 235 and a second adhesive ring 246 foam buttress is releasably attached to the movable second clamp member 245 respectively. The first initiator ring 236 contains an adhesive initiator 38, and the second adhesive ring 246 is a hollow cell foam containing the adhesive 48 sealed inside of a sealing surface 249 (See FIG. 7).

Turning now to FIGS. 7-10, the fixed clamp member 235 can include a plurality of deployable fasteners or staples 57 in a circular array of one or more concentric rings of staples 57 below the first initiator ring 236. A cylindrical knife 209 may be movably located within the fixed clamp member 235 inside of the array of staples 57. The movable second clamp member 245 could includes a plurality of staple forming pockets 247 behind the second adhesive ring 246.

Figure 7:
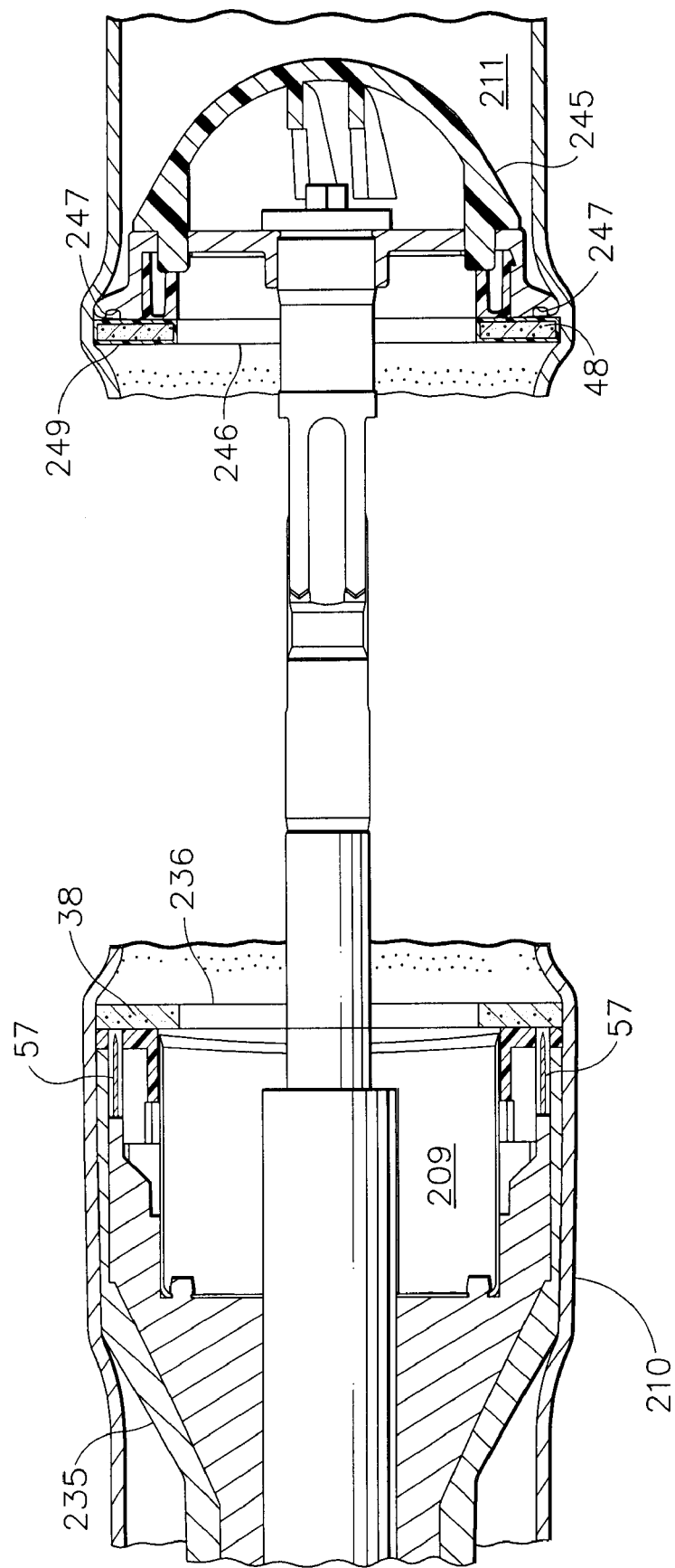
FIG. 7 is a cross sectional side view of the circular stapler of FIG. 6 showing a first step in creating an end-to-end anastomosis between two portions of severed intestinal tissue by placing the instrument in tissue.
Figure 8:
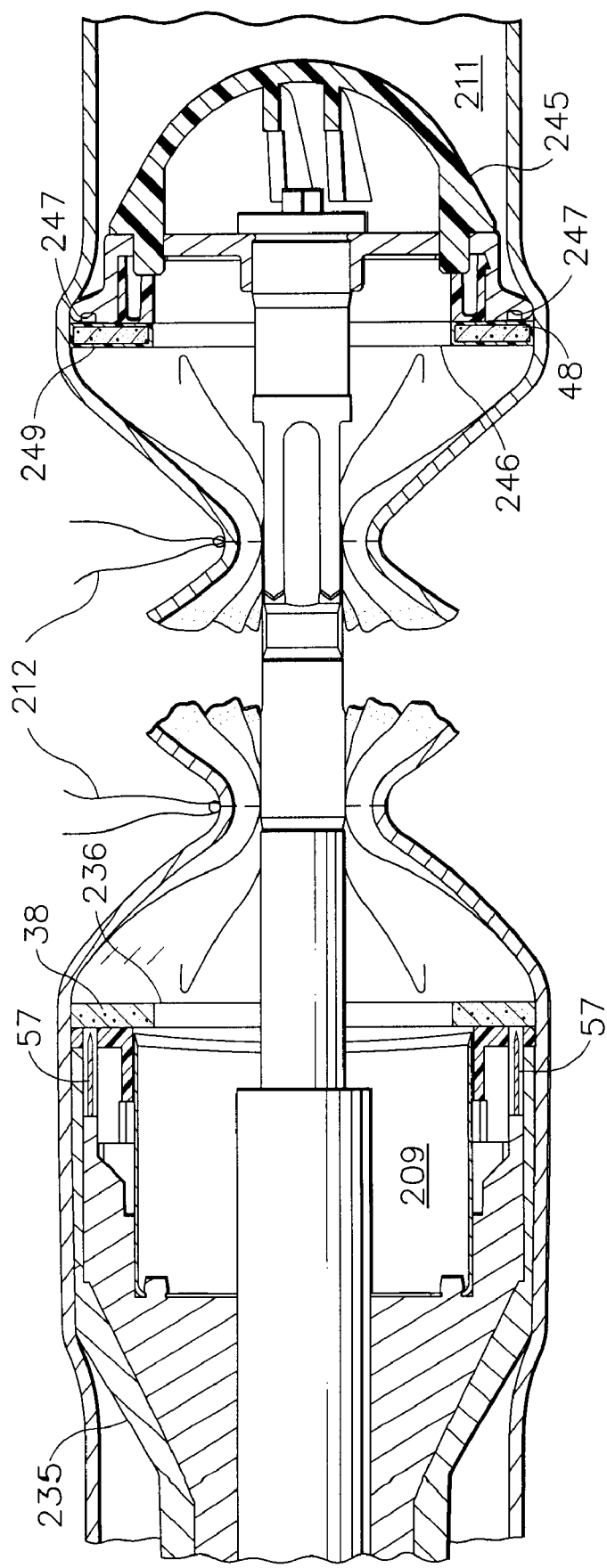
FIG. 8 is a cross sectional side view of the circular stapler of FIG. 7 showing a second step in creating an end-to-end anastomosis between two portions of severed intestinal tissue by creating purse strings in the tissue and drawing the tissue inward with the purse strings.
Figure 9:
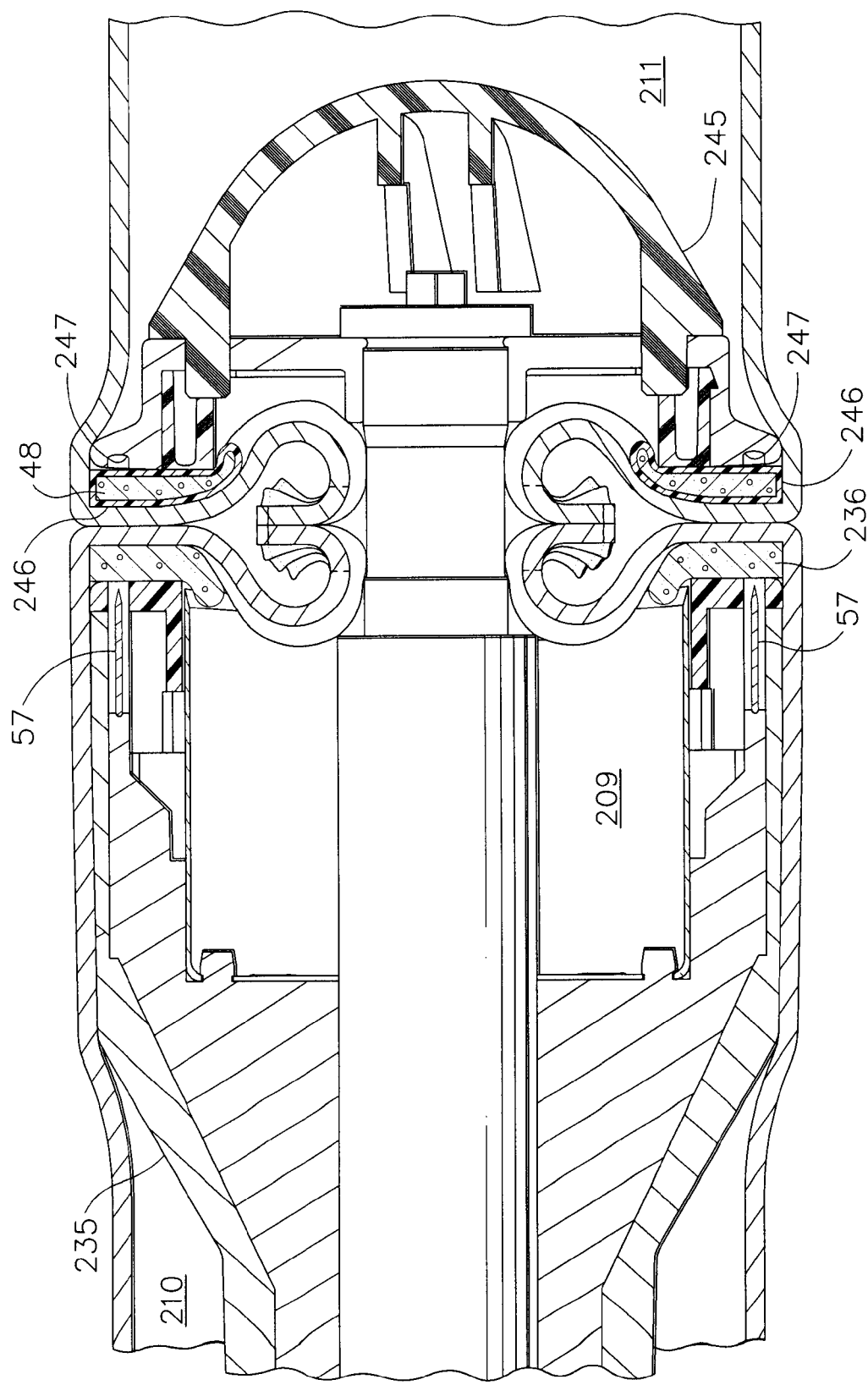
FIG. 9 is a cross sectional side view of the circular stapler of FIG. 8 showing a third step in creating an end-to-end anastomosis between two portions of severed intestinal tissue by closing the instrument to clamp tissue between the jaws.
Figure 10:
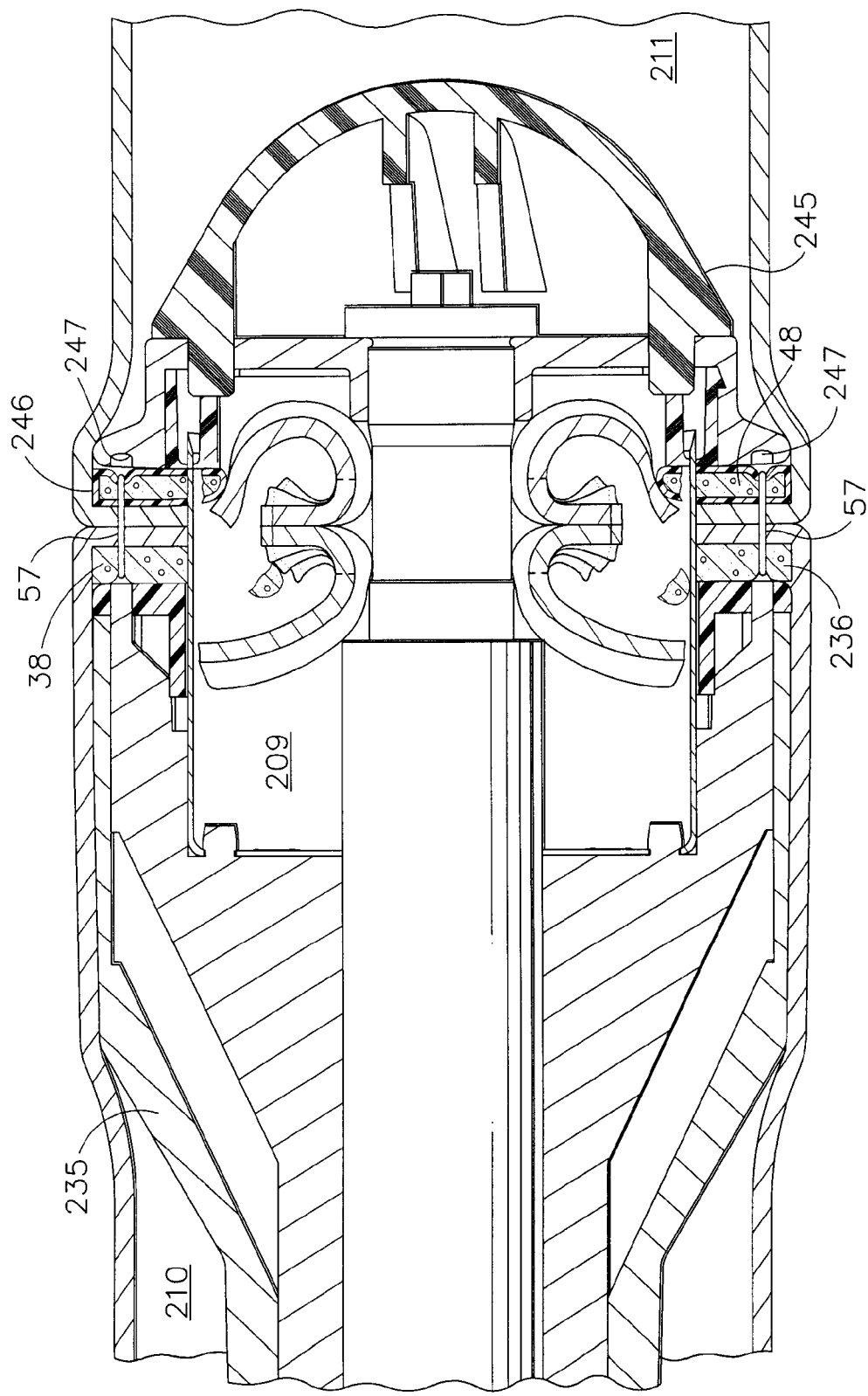
FIG. 10 is a cross sectional side view of the circular stapler of FIG. 9 showing a fourth step in creating an end-to-end anastomosis between two portions of severed intestinal tissue by firing the instrument to staple and cut both the tissue and the buttress, and to release the adhesive.

When the movable second clamp member 245 moves from the open position of FIGS. 6, 7 and 8, to a closed position of FIGS. 9 and 10, the staple forming pockets 247 to opposably align with the staples 57 in the fixed clamp member 235. Movable second clamp member 245 may be moved to the closed position of FIGS. 9 and 10 and back to the open position of FIGS. 6, 7 and 8 by rotating a knob 207 (FIG. 6) on the handle 205. Rotation of knob 207 in the opposite direction of knob 207 moves the movable second clamp member 245 to the open position. An actuatable firing trigger 208 (FIG. 6) may be provided to fire the circular stapler 225. When firing trigger 208 is fired, the staples 57 are driven into the tissue and formed in the staple pockets 247, and the tissue is cut with the knife 209.

A method of performing an anastomosis with circular stapler 225 and first initiator ring 236 and second adhesive ring 246 is shown in FIGS. 7-10. In FIG. 7, the circular end effector 230 has been inserted into a longitudinal slit (not shown) within the first portion of intestinal tissue 210, and moved into the position shown adjacent to an open end of the tissue 210. The movable second clamp member 245 may be moved to the open position and the second portion of intestinal tissue 211 can be inserted over the open movable second clamp member 245 as shown.

In FIG. 8, the intestinal tissue 210, 211 has been positioned as shown, and each portion of tissue 210, 211 has been fitted with a purse string of suture 212 placed about the open ends of the intestinal tissue. Each piece of suture 212 can be drawn tight to close the open ends of intestinal tissue 210, 211 and tied for security.

In FIG. 9, the movable second clamp member 245 has been closed to a position adjacent to the fixed clamp member 235 by rotating knob 207 to clamp the first and second portions of intestinal tissue 210, 211 therebetween. The clamping action is compressing the adhesive filled second adhesive ring 246, and expanded the second adhesive ring 246 inwardly.

In FIG. 10, the circular stapling device 225 can be shown fired by actuating the firing trigger 208. This action may moved the staples 57 out of the fixed clamp member 235 push them through the first initiator ring 236, through the first and second portions of intestinal tissue 210, 211, through the second adhesive ring 246 and form them in the staple pockets 247. The cylindrical knife 209 can have advanced past the first initiator ring 236, through the first and second portions of intestinal tissue 210, 211, and through the adhesive filled second adhesive ring 246. The knife 209 has released the adhesive 48 from the adhesive filled second adhesive ring 246 and the adhesive 48 is in contact with the outer surface of the knife.

Figure 11:
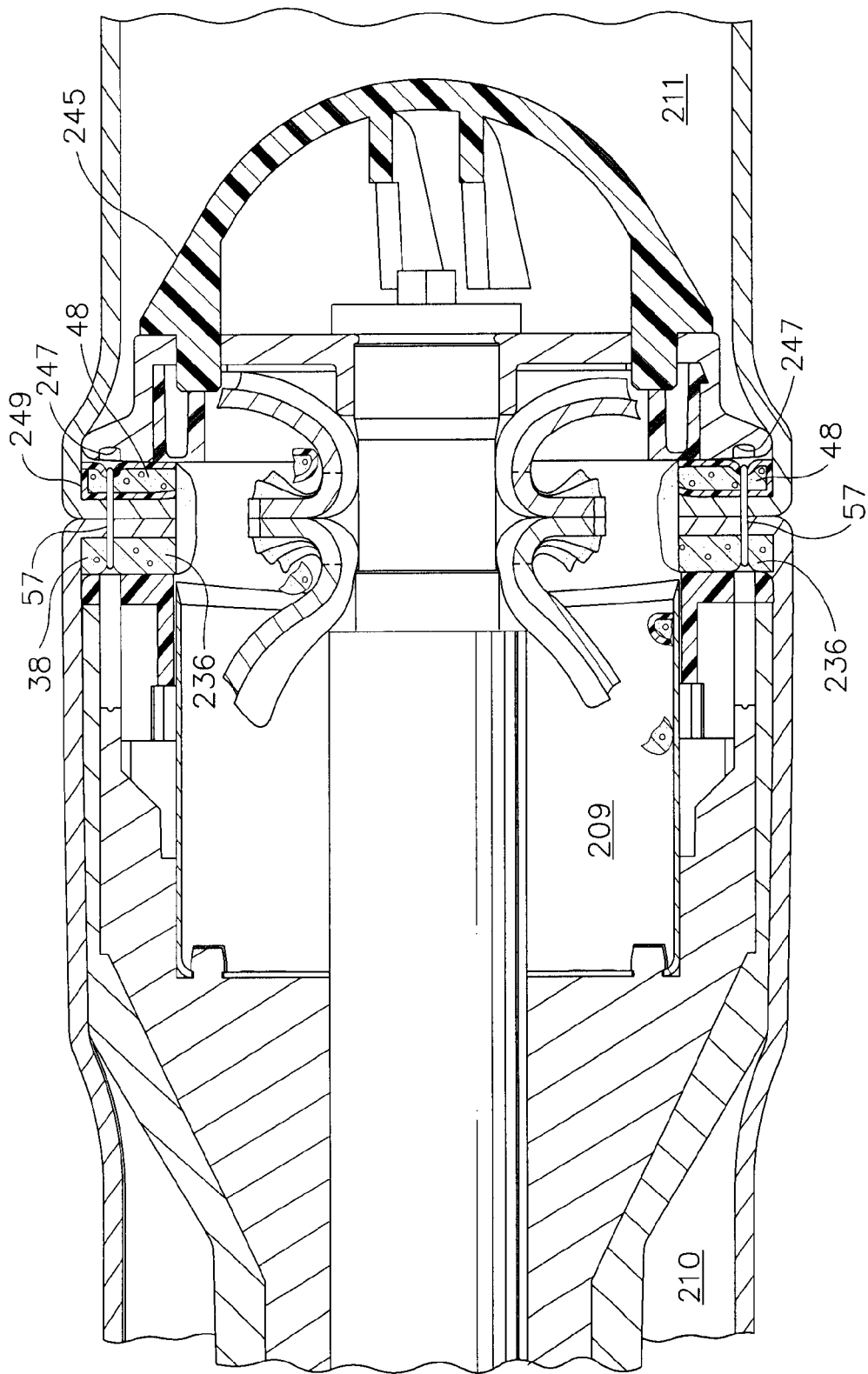
FIG. 11 is a cross sectional side view of the circular stapler of FIG. 10 showing a fifth step in creating an end-to-end anastomosis between two portions of severed intestinal tissue by returning the knife and applying the adhesive across the cut tissue and the buttress, wherein the adhesive initiator in the first portion of buttress is initiating setting or polymerization of the adhesive.

In FIG. 11, the firing trigger 208 may have been released to draw the knife back across the adhesive 48, to move the adhesive 48 across the severed ends of the intestinal tissue 210, 211, and move adhesive 48 into contact with the first initiator ring 236 containing the adhesive initiator 38. The adhesive initiator 38 can initiate the polymerization of the adhesive 48 smeared from the second adhesive ring 246, across the cut edges of the intestinal tissue 210, 211, and across the first initiator ring 236 to create a seal. The seal can prevent the migration of intestinal contents out of the intestine.

Alternately, the first initiator ring can be a matrix ring 236a impregnated with or coated with the adhesive initiator 38 (not shown). When the adhesive 48 contacts the adhesive initiator 38 on the matrix ring 236a, polymerization of the adhesive is initiated.

Figure 12:
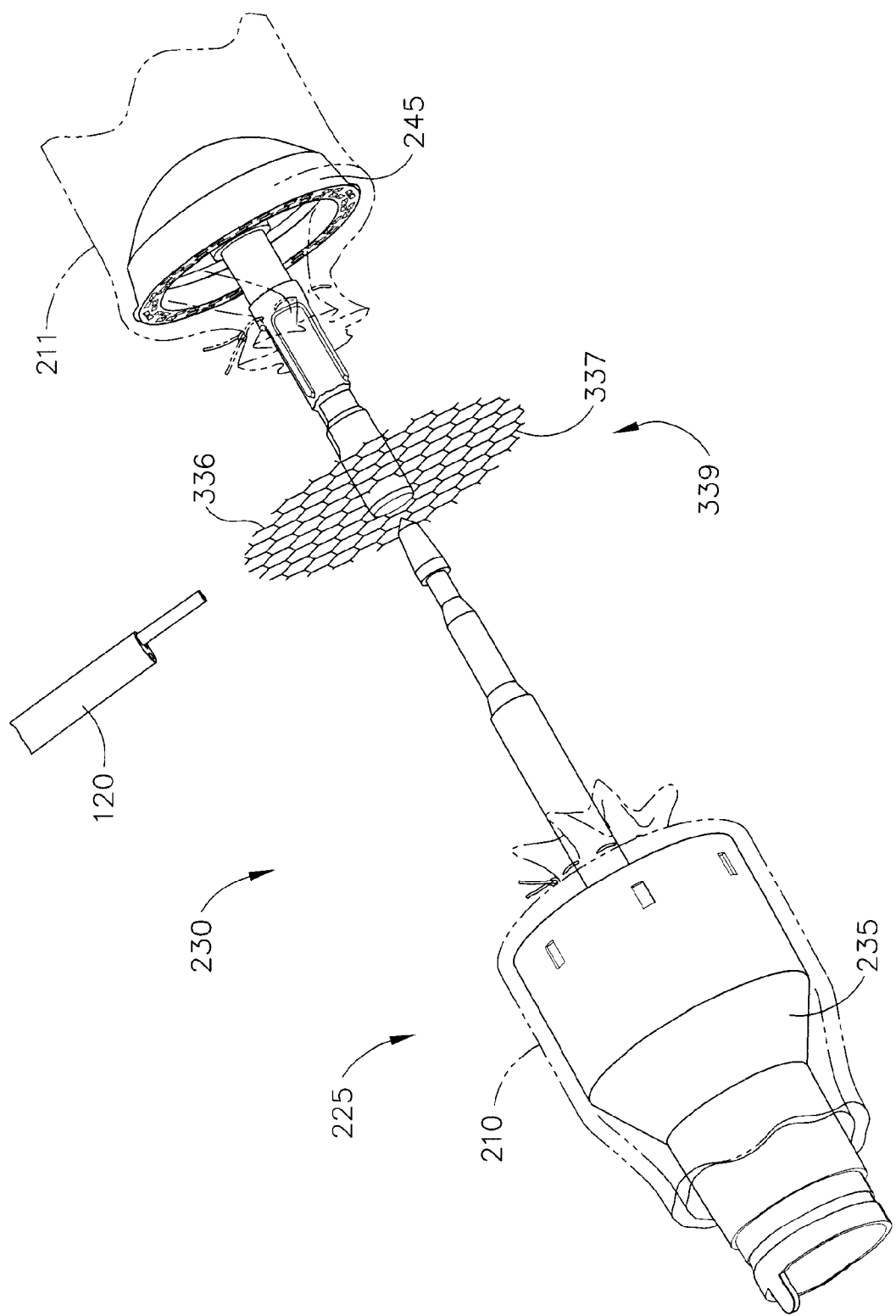
FIG. 12 is an isometric view of an alternate method of creating an end-to-end anastomosis between two portions of severed intestinal tissue by placing the instrument in tissue, and placing a single layer of a matrix between the two portions of tissue drawn inward by purse strings.
Figure 13:
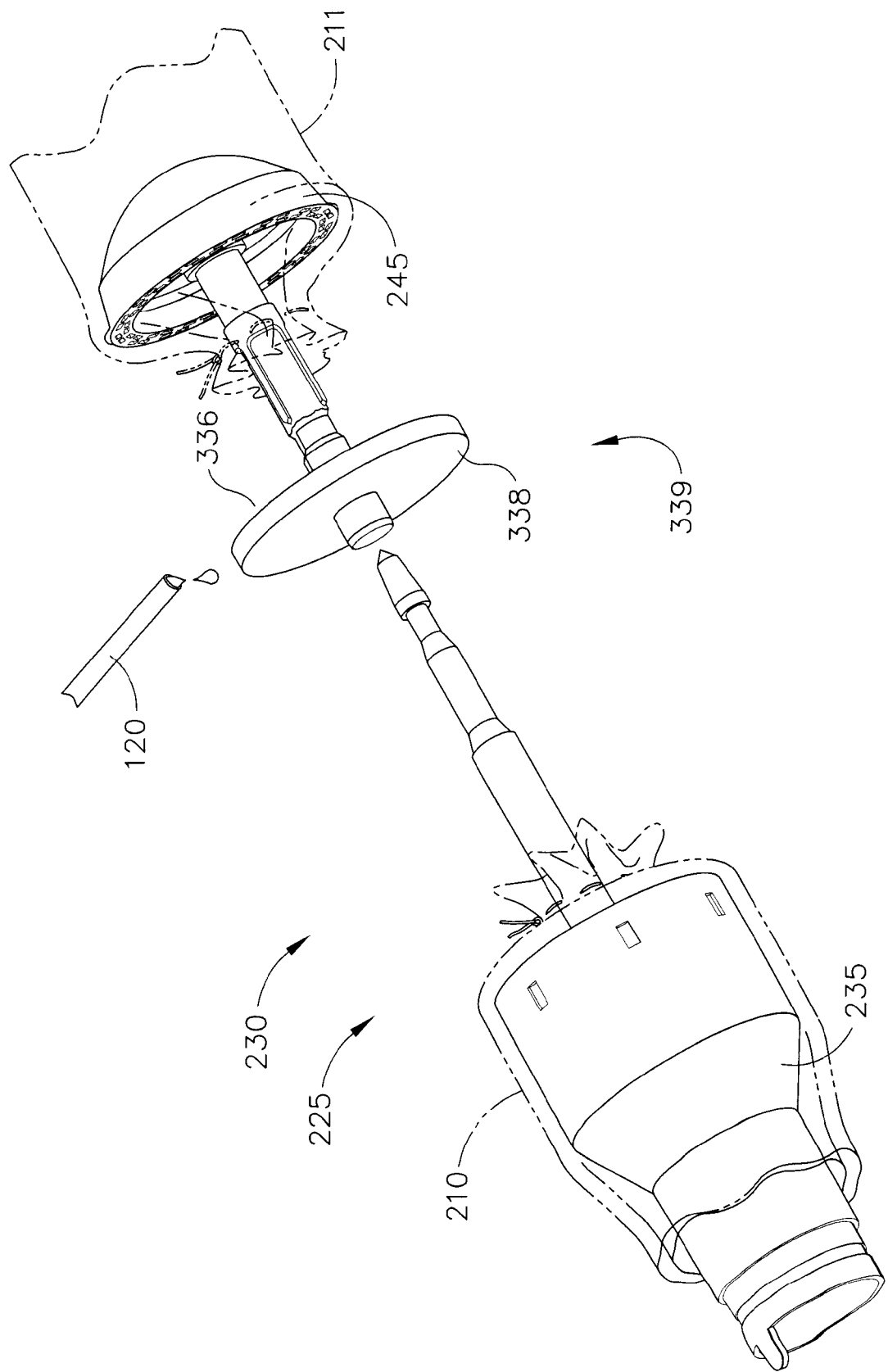
FIG. 13 is an isometric view of another alternate method of creating an end-to-end anastomosis between two portions of severed intestinal tissue by placing the instrument in tissue, and placing a single layer of a buttress disk between the two portions of tissue drawn inward by purse strings.
Figure 14:
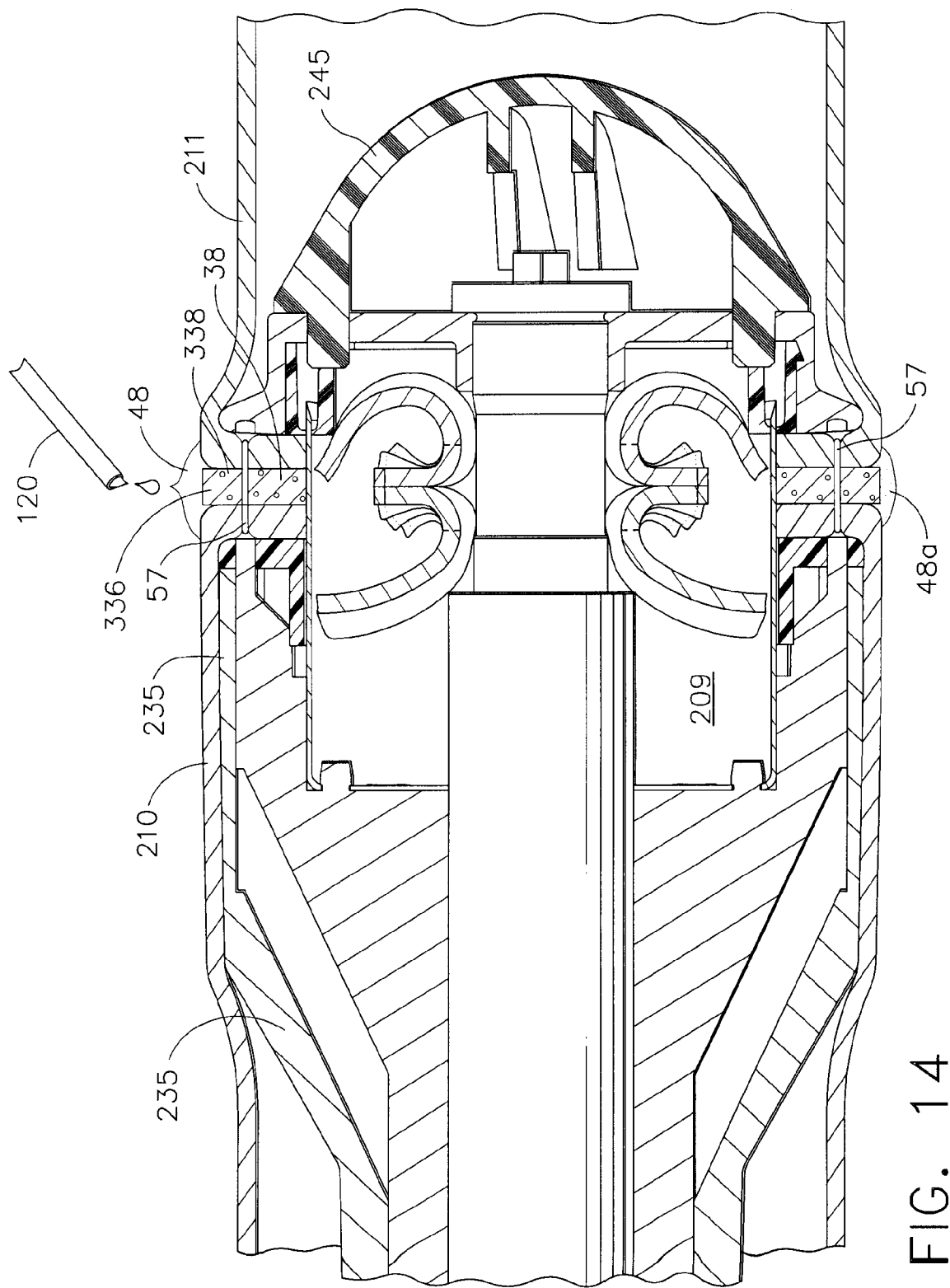
FIG. 14 is an isometric view of sealing an end-to end anastomosis between two portions of stapled and cut intestinal tissue with a portion of material containing an adhesive initiator therebetween and by placing adhesive onto the tissue and the portion of material containing the adhesive initiator to initiate polymerization of the adhesive and sealing of the anastomosis.

Alternate Embodiment of a Circular Stapler with a Single Portion of Buttress or Matrix FIGS. 12-14 can show an alternate embodiment of a method of using a single portion of material 339 containing an adhesive initiator 38 with the circular stapling device 225 and the adhesive 38 to create an end to end anastomosis of the first and second portions of intestinal tissue 210, 211. In FIG. 11, the single portion of material 336 can be a matrix or a buttress containing an adhesive initiator 38. Or, as shown in FIG. 12, the single portion of material 336 can be shown as a matrix 337 coated with or containing the adhesive initiator 38. In FIG. 13, the single portion of material 336 can be shown as a buttress disk 338 coated with or containing the adhesive initiator 38. Both the matrix 337 and the buttress disk 338 can be clamped between the portions of tissue 210, 211, and the circular stapler 225 fired to form staples through the first portion of tissue 210, the single portion of material 336, and through the second portion of material 211.

As shown in FIG. 14, the buttress disk 338 is impregnated with adhesive initiator 38 and can be clamped, stapled and cut between the first portion of intestinal tissue 210 and the second portion of intestinal tissue 211. An adhesive applicator 120 may be used to drip or apply adhesive to an exposed edge 337 of the buttress disk 338 where contact of the adhesive 48 with the initiator 38 can induce polymerization of the adhesive 48 to polymerized adhesive 48a. The polymerized adhesive 48a can seal the juncture of the first portion of intestinal tissue 210 and the second portion of intestinal tissue 211. Whereas FIG. 14 shows the example of a buttress disk 338 clamped between the tissue 210, 211, the matrix 337 with initiator 38 can also be used as an example for this procedure to initiate the polymerization of the adhesive from contact with the matrix 337 with initiator 38 to seal the tissue 210, 211 juncture It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, an adhesive filled sponge can have a coating to seal the adhesive therein and the coating can be coated with an adhesive initiator, or any other combination or embodiment of dispensable adhesive, adhesive initiator, and a buttress and/or matrix is within the scope of this invention to those skilled in the art.

What is claimed is:

1. A surgical stapling instrument for clamping and stapling tissue comprising:
   a) a handle, first and a second opposed tissue clamping members connected to the handle, at least one of the first and a second opposed tissue clamping members movable between an open position for receiving tissue and a closed position for stapling tissue therebetween, the first clamping member including a plurality of staples disposed therein in an array, the second clamping member comprising an anvil for forming the staples;
   b) a first portion of biocompatible material into which an adhesive initiator is incorporated, the first portion of biocompatible material being releasably attached to one of the first and second opposed tissue clamping members;
   c) a second portion of biocompatible material into which a fluid adhesive is incorporated, the second portion of biocompatible material being releasably attached to the other of the first and second opposed tissue clamping members and wherein the fluid adhesive polymerizes when in contact with the adhesive initiator; and
   d) a knife operably movable between the first and a second opposed tissue clamping members, wherein when the tissue is clamped and stapled, the knife cuts through the tissue, the first portion of biocompatible material that incorporates the adhesive initiator, and the second portion of biocompatible material that incorporates the fluid adhesive to release the adhesive, and wherein the cut provides a passage for migration of the adhesive from the second portion of material to the adhesive initiator in the first portion of material to initiate hardening of the adhesive across the cut.

2. The surgical device of claim 1 wherein the first portion of biocompatible material and the second portion of biocompatible material is one or more selected from the group consisting of:
   a) a buttress;
   b) a matrix having a plurality of openings therein;
   c) an open cell foam;
   d) a closed cell foam; and
   e) a fabric pad.

3. The surgical device of claim 2 wherein one or more of the first portion of biocompatible material and the second portion of biocompatible material is absorbable.

4. The surgical device of claim 2 wherein one or more of the first portion of biocompatible material and the second portion of biocompatible material includes at least one wicking feature.

5. The surgical device of claim 1 wherein the second portion of biocompatible material has a seal to hold the adhesive within, wherein the seal is one selected from the group consisting of:
   a) a surface skin on the material;
   b) a pouch;
   c) a coating;
   d) a gelatin; and
   e) an absorbable biocompatible material.

6. The surgical device of claim 1 wherein the array of the plurality of staples is a one or more selected from the group consisting of:
   a) a circular array;
   b) an array of one or more rows; and
   c) an arcuate array.

7. The surgical device of claim 1 wherein the adhesive is one or more selected from the group consisting of a polymerizable monomer, a polymerizable 1,1,1,1-disubstituted ethylene monomer, and a cyanoacrylate formulation.

8. The surgical device of claim 1 wherein the adhesive initiator is incorporated into the first portion of biocompatible material in one or more manners selected from the group consisting of:
   a) as a coating;
   b) combined with the first portion of biocompatible material; and
   c) contained within the first portion of biocompatible material.

9. The surgical device of claim 1 wherein the first portion of biocompatible material and the second portion of biocompatible material is one or more selected from the group consisting of epsilon.-caprolactone glycolide, bovine pericardium, polylactic acid, polyglycolic acid, polyglactin, polydioxanone, polyglyconate, whey protein, cellulose gum, starch, gelatin, silk, nylon, polypropylene, braided polyester, polybutester, polyethylene, and polyetheretherketones.

10. A method for securing a first and a second portion of tissue together with a plurality of staples and an adhesive comprising:
   a) placing a portion of material into which an adhesive initiator is incorporated between a first portion and a second portion of tissue;

b) clamping the material incorporating the adhesive initiator and the first and second portion of tissue between a first and a second clamping member of a surgical device with at least an edge of the material exposed;
c) stapling the two portions of tissue together with the portion of material incorporating the adhesive initiator therebetween with the plurality of staples in an array; and
d) applying an adhesive about the at least one exposed edge of material and the two portions of tissue to initiate the adhesive through contact between the adhesive and the adhesive initiator and to secure the two portions of tissue together.

11. The method of claim 10 wherein the step of stapling the two portions of tissue together includes cutting the tissue and the material with the surgical device.

12. The method of claim 11 further comprising removing the tissue from the surgical device before applying the adhesive across the cut.

13. The method of claim 10 wherein the step of applying an adhesive about the exposed material and the two portions of tissue includes placing the adhesive across the cut.

14. The method of claim 10 wherein the portion of material into which the adhesive initiator is incorporated includes at least one wicking feature and wherein after the step of applying an adhesive about the at least one exposed edge of material, the adhesive is drawn about the portion of material and into contact with the adhesive initiator by wicking action.

15. The method of claim 10 wherein the step of applying an adhesive includes creating a seal.

16. The method of claim 10 wherein the step of stapling the clamped material includes forming the staples in a linear array.

17. The method of claim 10 wherein the step of stapling the clamped material includes forming the staples in a circular array.

* * * * *